United States Patent
Bielby (10) Patent No.: US 11,091,166 B1
(45) Date of Patent: Aug. 17, 2021

(54) DRIVER SCREENING

(71) Applicant: Micron Technology, Inc., Boise, ID (US)

(72) Inventor: Robert Richard Noel Bielby, Placerville, CA (US)

(73) Assignee: Micron Technology, Inc., Boise, ID (US)

(*) Notice: Subject to any disclaimer, the term of this patent is extended or adjusted under 35 U.S.C. 154(b) by 0 days.

(21) Appl. No.: 16/854,634

(22) Filed: Apr. 21, 2020

(51) Int. Cl.
| | |
|---|---|
| *B60W 40/09* | (2012.01) |
| *G06K 9/00* | (2006.01) |
| *G06T 7/73* | (2017.01) |
| *G06N 3/08* | (2006.01) |
| *B60R 11/04* | (2006.01) |
| *B60R 11/02* | (2006.01) |
| *B60W 40/08* | (2012.01) |

(52) U.S. Cl.
CPC ......... *B60W 40/09* (2013.01); *B60R 11/0247* (2013.01); *B60R 11/04* (2013.01); *G06K 9/00845* (2013.01); *G06K 9/00892* (2013.01); *G06N 3/084* (2013.01); *G06T 7/74* (2017.01); *B60R 2300/408* (2013.01); *B60W 2040/089* (2013.01); *B60W 2040/0836* (2013.01); *B60W 2040/0872* (2013.01); *B60W 2540/223* (2020.02); *B60W 2540/24* (2013.01); *G06T 2207/20084* (2013.01); *G06T 2207/30201* (2013.01)

(58) Field of Classification Search
CPC ........... B60W 40/09; B60W 2540/223; B60W 2540/24; B60W 2040/0836; B60W 2040/089; B60W 2040/0872; G06K 9/00845; G06K 9/00892; G06N 3/084
See application file for complete search history.

(56) References Cited

U.S. PATENT DOCUMENTS

| | | | |
|---|---|---|---|
| 10,322,728 B1* | 6/2019 | Porikli | G06K 9/6288 |
| 10,713,948 B1* | 7/2020 | Kim | G06K 9/00248 |
| 2009/0164069 A1* | 6/2009 | Yanagisawa | B60K 28/063 701/45 |
| 2014/0168399 A1* | 6/2014 | Plummer | G06Q 40/08 348/78 |
| 2016/0311440 A1* | 10/2016 | Gan | G08B 21/06 |
| 2017/0102783 A1* | 4/2017 | Shikii | G06F 3/012 |
| 2017/0369069 A1* | 12/2017 | Yen | B60T 7/18 |
| 2018/0032944 A1* | 2/2018 | Sarvana | G06Q 10/063114 |
| 2018/0089605 A1* | 3/2018 | Poornachandran | G06Q 30/0282 |
| 2018/0174457 A1* | 6/2018 | Taylor | G06K 9/00302 |
| 2020/0207358 A1* | 7/2020 | Katz | G06K 9/00845 |

* cited by examiner

*Primary Examiner* — Andrew W Bee
(74) *Attorney, Agent, or Firm* — Greenberg Traurig (57) ABSTRACT

A vehicle having one or more cameras, configured to record one or more images of a driver of the vehicle. The camera(s) can be configured to send biometric image data derived from the image(s). The vehicle can include a computing system configured to receive the biometric data and to determine a risk score of the driver based on the received biometric data and an AI technique, such as an ANN or a decision tree. The received biometric data or a derivative thereof can be input for the AI technique. The computing system can also be configured to transmit the risk score of the driver to the customer so that the customer can decide whether to book the vehicle for a ride.

20 Claims, 6 Drawing Sheets

DRIVER SCREENING

FIELD OF THE TECHNOLOGY

At least some embodiments disclosed herein relate to a networked system for driver screening. For example, at least some embodiments disclosed herein relate to a network system for driver screening for ridesharing services.

BACKGROUND

Ridesharing has become a pervasive mode of transportation in the United States and is growing throughout the world. A ridesharing service connects passengers with drivers or vehicles via a website or another type of application. Currently, several ridesharing services match customers and vehicles via mobile apps. Ridesharing services for automobiles can be referred to as ride-hailing services, and such services also are available for ridesharing with other types of vehicles including aircraft and watercraft.

Ridesharing services have become prevalent in less populated or poorer areas that are not regularly served by taxicabs. Also, ridesharing has become widespread because there is at least a perception that such services are less expensive than taxicab services. Also, ridesharing is beneficial because it has been shown to reduce drunk driving rates in some cities where such services operate.

One example problem with ridesharing is that it is at least perceived to be less safe than hailing a taxi or a professional ride service. However, steps are being made to overcome safety concerns as well as concerns of fraudulent ridesharing services. On the other hand, intoxicated, fraudulent, or belligerent customers can create problems for drivers. Also, tired, drunk, deceitful, or aggressive drivers can create problems for customers.

To protect drivers as well as customers, ridesharing services have been regulated in cities, states, and countries. And, in some jurisdictions, ridesharing has been banned due to safety concerns and possibly lobbying by taxi companies. Regulations for ridesharing services can include requirements for driver background checks, fares, the number of drivers, licensing, and driver wage.

BRIEF DESCRIPTION OF THE DRAWINGS

The present disclosure will be understood more fully from the detailed description given below and from the accompanying drawings of various embodiments of the disclosure.

DETAILED DESCRIPTION

At least some embodiments disclosed herein relate to a networked system for driver screening. For example, at least some embodiments disclosed herein relate to a network system for driver screening for ridesharing services. In some embodiments, a taxicab or a vehicle of a ridesharing service can take pictures or record a video of a driver inside the taxicab or vehicle and generate a risk score of the driver. The risk score can relate to whether or not the driver is too tired, intoxicated, or unstable to drive. The score can even relate to an intoxication level or tiredness level of the driver as well as the mental state or stability of the driver. The score can also relate to physical or cognitive impairment of the driver, criminal history of the driver and riding history of the driver. The customer, via a mobile device, can be presented the risk score when booking a ride. Also, the rider can be alerted or prompted to refuse the driver when the risk score is above a threshold. This can occur when the customer is using the mobile device to book a ride. To put it another way, in booking a taxi or ridesharing, a vehicle can take pictures of the driver and evaluate the performance readiness level of the driver (e.g., whether the driver is tired, slow in response, intoxicated, the current performance level relative to peak performance level, driving style, etc.). The evaluation can then be transmitted to the potential customer of the taxi or ridesharing during the decision of whether to book the driver for a ride.

In some embodiments, the networked system for driver screening uses artificial intelligence (AI) in generating a risk score. An AI technique, such as an artificial neural network (ANN), convolutional neural network (CNN), etc., can be trained to recognize patterns in input data and generate risk scores. Where traditional linear computer programming techniques follow strict rules, AI techniques, such as ANN, CNN, etc., can use machine learning to learn and adapt with changing inputs. This ability to learn and adapt with changing inputs can make AI techniques useful components of a networked system for driver screening.

In general, an ANN may be trained using a supervised method where the parameters in the ANN are adjusted to minimize or reduce the error between known outputs resulted from respective inputs and computed outputs generated from applying the inputs to the ANN. Examples of supervised learning/training methods include reinforcement learning, and learning with error correction.

Alternatively, or in combination, an ANN may be trained using an unsupervised method where the exact outputs resulting from a given set of inputs are not known before the completion of training. The ANN can be trained to classify an item into a plurality of categories, or data points into clusters. Multiple training algorithms can be employed for a sophisticated machine learning/training paradigm.

In some embodiments, to train the system of a ridesharing service for a particular user, a customer or passenger can look at sample images of drivers and give respective risk scores. The system can then use artificial intelligence to learn to provide risk scores similarly to the customer or to ridesharing customers of the service in general based on such input. The learning (or machine learning) can be done using a dataset such as sets of images of drivers and corresponding risk scores. For example, if a customer is given the opportunity to determine a risk score of a driver by observing the driver for a moment (e.g., using the ridesharing app of the system), what the customer or passenger observed can be similarly observed by a camera. The system cannot determine how a customer decides on a risk score; but, the system can train or adjust parameters of an AI technique, such as an ANN, CNN or a decision tree, to minimize the difference between the risk scores generated by the customer (or customers of the service in general) and the scores computed by the AI technique. Datasets input to the AI technique can be made more complex by adding other biometric inputs (e.g., sound from speech, alcohol content from a breathalyzer, body temperature, etc.) With each additional dataset, the AI technique continues to learn, adapt, and refine the risk score. Such machine learning can be considered supervised machine learning.

In some embodiments, a vehicle can include at least one camera, configured to record at least one image of a driver in the vehicle during a time period. The camera(s) can also be configured to send image data derived from the at least one image of the driver. The recording of the at least one image can occur in response to a request for an evaluation of the driver by a customer determining whether to book the vehicle for a ride. The request can occur during the time period.

The vehicle can also include a computing system, configured to receive the image data from the at least one camera and determine a risk score of the driver for the time period based on the received image data and an AI technique. The AI technique can include an ANN, a decision tree, or another type of AI tool, or any combination thereof. The received biometric data or a derivative thereof can be input for the AI technique in general or specifically for an ANN, a decision tree, or another type of AI tool, or any combination thereof. The computing system can also be configured to transmit the risk score of the driver to the customer so that the customer can decide whether to book the vehicle for a ride.

In some embodiments, the vehicle can include at least one sensor configured to sense at least one non-visual biometric feature of the driver during the time period and send non-visual biometric data derived from the at least one sensed non-visual biometric feature of the driver. In such embodiments and others, the computing system can be configured to receive the non-visual biometric data from the at least one sensor and determine the risk score of the driver for the time period based on the received image data, the received non-visual biometric data and the AI technique. The received non-visual biometric data or a derivative thereof can be input for the AI technique in general or specifically for an ANN, a decision tree, or another type of AI tool, or any combination thereof.

In some embodiments, the at least one sensor can include a breathalyzer configured to sense blood alcohol content of the driver during the time period, and the at least one sensor is configured to send data derived from the sensed blood alcohol content as at least part of the non-visual biometric data. In such embodiments and others, the at least one sensor can include a thermometer configured to sense a body temperature of the driver during the time period, and the at least one sensor can be configured to send data derived from the sensed body temperature as at least part of the non-visual biometric data. In such embodiments and others, the at least one sensor can include a microphone configured to transform sound from speech of the driver during the time period into an audio signal, and the at least one sensor can be configured to send data derived from the audio signal as at least part of the non-visual biometric data.

In some embodiments, the received image data sent from the at least one camera can include information on a posture of the driver. And, in such embodiments and others, the received image data sent from the at least one camera can include information on facial characteristics of the driver.

In some embodiments, the computing system of the vehicle is configured to train the AI technique using supervised learning. The input for the supervised learning of the AI technique can include image data of images of sample drivers and risk scores determined by the customer for the images of the sample drivers. This way the AI technique (such as an ANN or a decision tree) can be customized and trained for the customer specifically. Also, the input for the supervised learning of the AI technique can include image data of images of sample drivers and risk scores determined by customers of the ridesharing service for the images of the sample drivers. This way the AI technique can be enhanced and trained for the customers of the service in general. The input for the supervised learning of the ANN can also include non-visual biometric information of the sample drivers and risk scores determined by the customer (or customers of the service in general) for the non-visual biometric information of the sample drivers.

In some embodiments, the computing system of the vehicle is configured to determine, via a ridesharing service app of a ridesharing service, biographical information of the driver of the vehicle based on at least the received biometric data and/or a database of drivers of the ridesharing service. The database can store biographical information on registered drivers that are registered for the ridesharing service. And, the stored biographical information can include biometric characteristics of the registered drivers as well as at least one of criminal histories of the registered drivers, driving behavior histories of the registered drivers, or service or traffic violation histories of the registered drivers, or any combination thereof. In such embodiments and others, the computing system of the vehicle can be configured to determine the risk score of the driver based on the received biometric data, the AI technique, and the determined biographical information of the driver. The input for the AI technique can include the biometric data or a derivative thereof and/or the determined biographical information or a derivative thereof.

Figure 1:
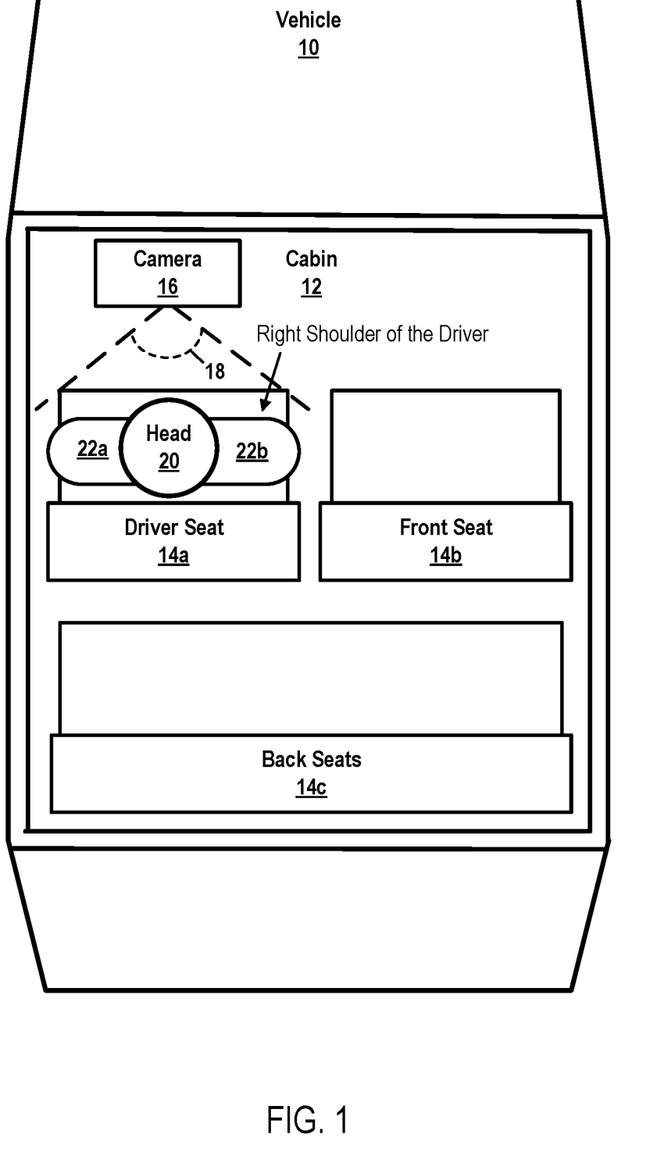
FIG. 1 illustrates a diagram of an example vehicle configured to implement aspects of driver screening for ridesharing services, in accordance with some embodiments of the present disclosure.

FIG. 1 illustrates a diagram of an example vehicle 10 configured to implement aspects of driver screening for ridesharing services, in accordance with some embodiments of the present disclosure. As shown in FIG. 1, the vehicle 10 includes a cabin 12 and the cabin includes a driver seat 14a, another front seat 14b, and back seats 14c. The cabin 12 also includes a camera 16 facing the driver seat 14a. The camera 16 has an angle of view 18, which appears to be less than one hundred and eighty degrees in the embodiment shown in FIG. 1. The angle of view 18 allows for the camera 16 to record at least one image or a video of a driver sitting in the driver seat 14a. As shown, the angle of view 18 provides for a field of view including the head 20 of the driver as well as the right shoulder 22b and the left shoulder 22a of the driver. As shown, the camera 16 faces away from the front of the vehicle 10 or the windshield of the vehicle (the windshield is not depicted in FIG. 1).

The camera 16 is shown as being in the cabin 12 of the vehicle 10. However, it is to be understood that such a camera for recording the driver can be located and attached to the vehicle 10 at any part of the vehicle as long as the camera is positioned in a way to capture images or a video recording of the driver in the driver seat 14a. As shown, FIG. 1 depicts a top sectional view of the vehicle 10 below the roof of the body of the vehicle so that the cabin 12 of the vehicle is shown. Also, as shown in FIG. 1, the camera 16 is not a panorama camera configured to record images from a wide horizontal angle; however, in some embodiments, the camera 12 can be a panorama camera. It is to be understood that the angle of view of such a camera for recording image(s) of the driver can be of any degrees as long as the camera's field of view covers a sufficient area to capture behavior of the driver or characteristics of the driver in the driver seat.

Also, it is to be understood that a different number of cameras can be used, and cameras with different or same viewing angles can be used, as well as the viewing fields of the cameras in the horizontal plane may or may not overlap in some embodiments. Also, in some embodiments, the vehicle can include one or more omnidirectional cameras to cover at least a full circle in the horizontal plane relative to the inside of the cabin of the vehicle or to cover a field of view with a full or nearly full sphere inside of the cabin of the vehicle. Such embodiments can be useful for capturing features or behaviors of the driver from other locations in the cabin of the vehicle besides the driver seat.

Figure 2:
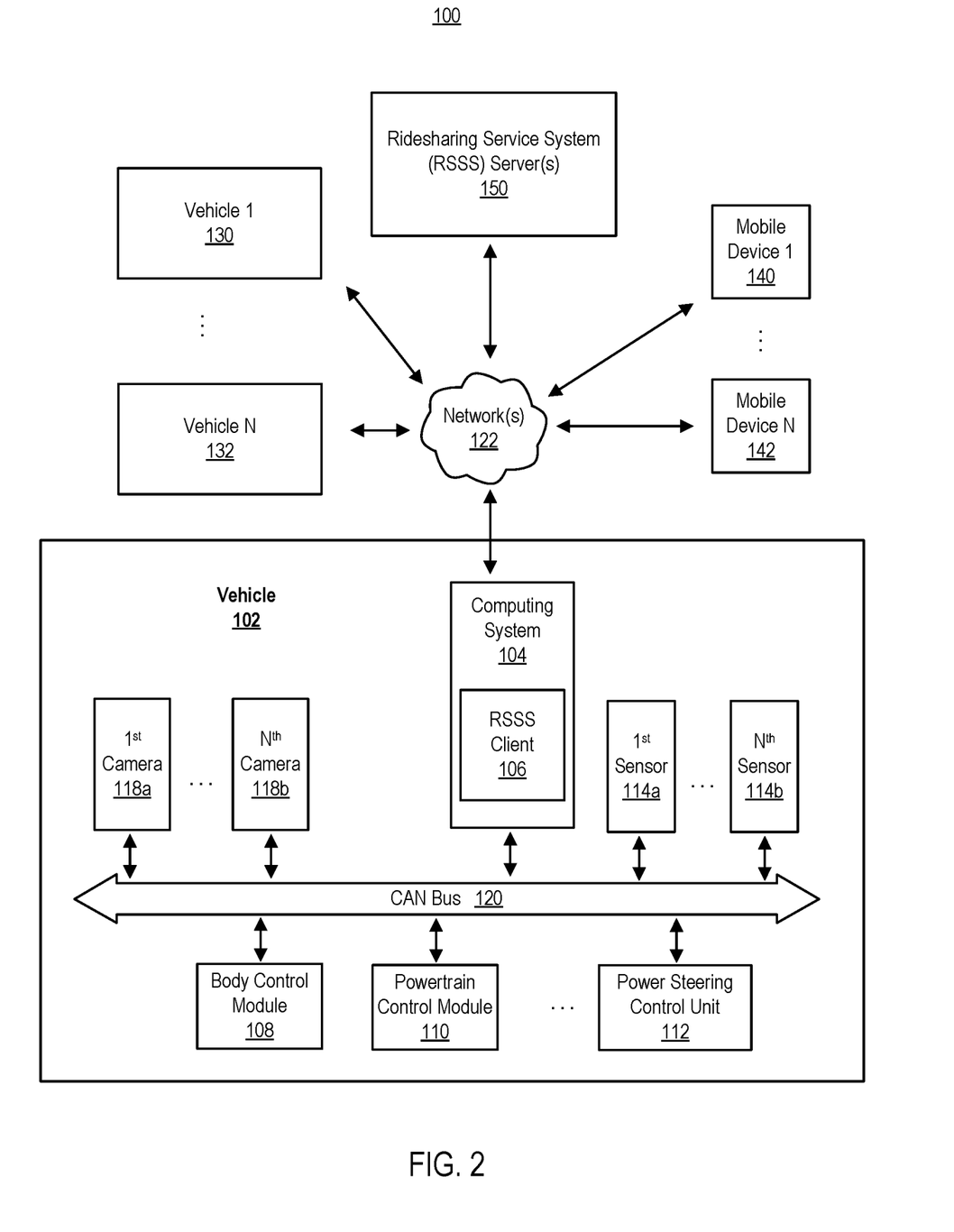
FIGS. 2 to 4 illustrate an example networked system that includes at least mobile devices and vehicles as well as a ridesharing service system (RSSS) and that is configured to implement driver screening for ridesharing services, in accordance with some embodiments of the present disclosure.
Figure 3:
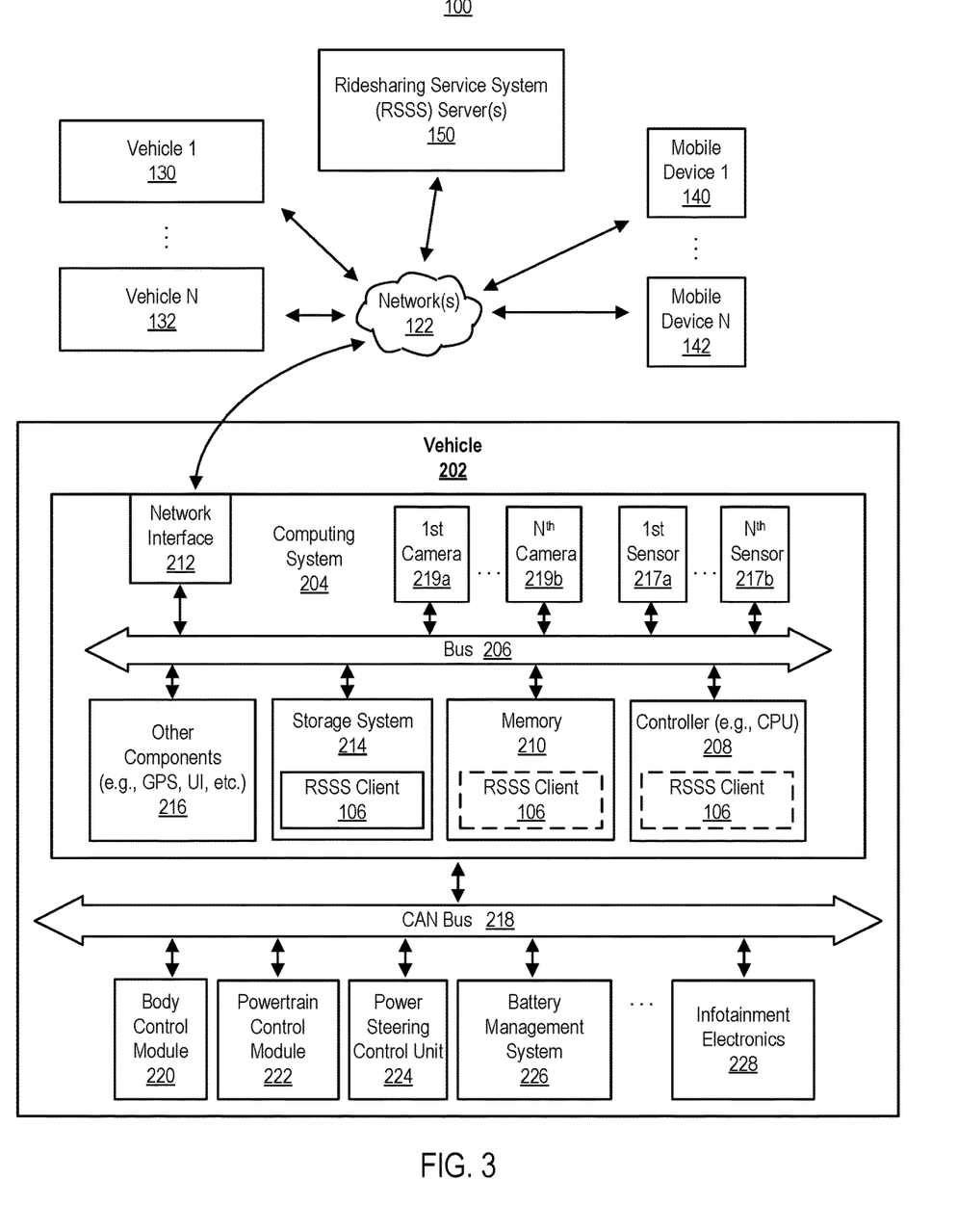
Figure 4:
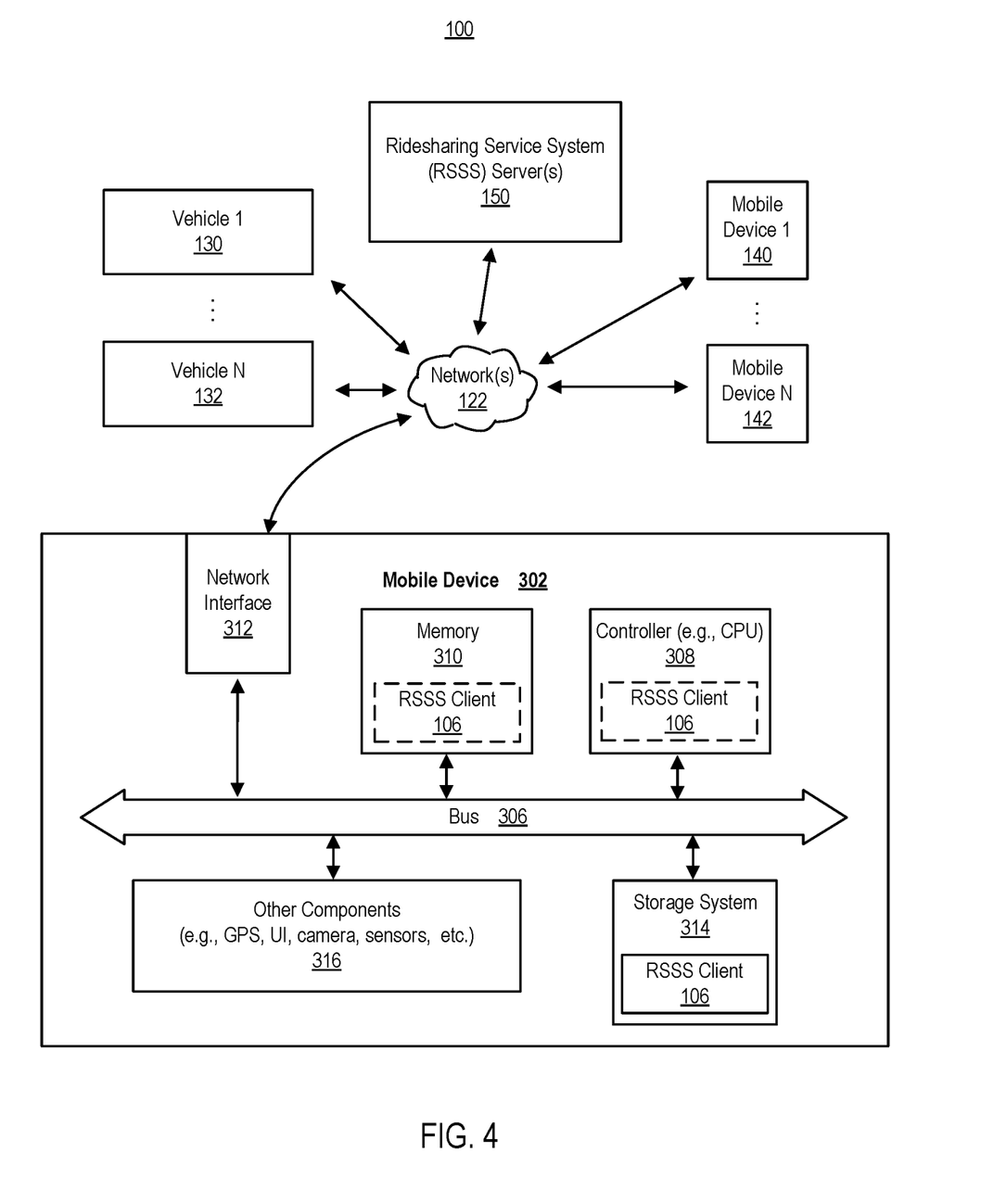

FIGS. 2 to 4 illustrate an example networked system 100 that includes at least a ridesharing service system (RSSS) as well as mobile devices and vehicles (e.g., see mobile devices 140 to 142 and 302 and vehicles 102, 202, and 130 to 132) and that is configured to implement driver screening for ridesharing services, in accordance with some embodiments of the present disclosure. Any one or more of the vehicles 102, 202, and 130 to 132 can be the vehicle 10 shown in FIG. 1 or include at least some of the parts of the vehicle 10.

The networked system 100 is networked via one or more communications networks 122. Communication networks described herein, such as communications network(s) 122, can include at least a local to device network such as Bluetooth or the like, a wide area network (WAN), a local area network (LAN), the Intranet, a mobile wireless network such as 4G or 5G, an extranet, the Internet, and/or any combination thereof. Nodes of the networked system 100 (e.g., see mobile devices 140, 142, and 302, vehicles 102, 130, 132, and 202, and one or more RSSS servers 150) can each be a part of a peer-to-peer network, a client-server network, a cloud computing environment, or the like. Also, any of the apparatuses, computing devices, vehicles, sensors or cameras, and/or user interfaces described herein can include a computer system of some sort (e.g., see vehicle computing systems 104 and 204). And, such a computer system can include a network interface to other devices in a LAN, an intranet, an extranet, and/or the Internet. The computer system can also operate in the capacity of a server or a client machine in client-server network environment, as a peer machine in a peer-to-peer (or distributed) network environment, or as a server or a client machine in a cloud computing infrastructure or environment.

As shown in FIG. 2, the networked system 100 can include at least a vehicle 102 that includes a vehicle computing system 104 (including a client application 106 of the RSSS—also referred to herein as the RSSS client 106), a body and controllable parts of the body (not depicted), a powertrain and controllable parts of the powertrain (not depicted), a body control module 108 (which is a type of electronic control unit or ECU), a powertrain control module 110 (which is a type of ECU), and a power steering control unit 112 (which is a type of ECU). The vehicle 102 also includes a plurality of sensors (e.g., see sensors 114a to 114b—which can include biometric sensors), a plurality of cameras (e.g., see cameras 118a to 118b—which can include camera 16 shown in FIG. 1), and a controller area network (CAN) bus 120 that connects at least the vehicle computing system 104, the body control module 108, the powertrain control module 110, the power steering control unit 112, the plurality of sensors, and the plurality of cameras to each other. Also, as shown, the vehicle 102 is connected to the network(s) 122 via the vehicle computing system 104. Also, shown, vehicles 130 to 132 and mobile devices 140 to 142 are connected to the network(s) 122. And, thus, are communicatively coupled to the vehicle 102.

The RSSS client 106 included in the vehicle computing system 104 can communicate with the RSSS server(s) 150. The RSSS client 106 can be or include an RSSS client specifically configured for use by the customer of the ridesharing service. Also, the RSSS client 106 can be or include an RSSS client specifically configured for use by the driver of the ridesharing service.

In some embodiments, the vehicle 102 can include a body, a powertrain, and a chassis, as well as at least one camera and at least one sensor (e.g., see cameras 118a to 118b and sensors 114a to 114b). The at least one camera and at least one sensor can each be attached to at least one of the body, the powertrain, or the chassis, or any combination thereof. For example, the camera(s) or sensor(s) can be embedded in or attached to a ceiling of the body of the vehicle 102, a sidewall of a cabin of the body, a door of the body, a front part of the cabin of the body, or a back part of the cabin of the body (such as in or near a back seat of the cabin). The camera(s) or sensor(s) can be configured to face inwards into the cabin of the vehicle 102 and to capture, sense, or record a field of view that covers up to a semi-circle or a full circle in a horizontal plane relative to the vehicle to capture at least one image or non-visual biometric information of a driver within the cabin of the vehicle.

In such embodiments and others, the vehicle 102 includes at least one camera (e.g., see cameras 118a to 118b) configured to record at least one image of a driver in the vehicle. The recording by the at least one camera can occur during a time period. And, the at least one camera can be configured to generate and send biometric image data derived from the at least one image of the driver. The recording of the at least one image can occur in response to a request for an evaluation of the driver by a customer determining whether to book the vehicle 102 for a ride. And, the recording of the at least one image can occur during the time period in which request is made by the customer. In other words, the request can occur during the time period of the recording of the at least one image of the driver. And, the customer can make the request from a mobile device (e.g., see mobile devices 140 to 142 and mobile device 302).

In such embodiments and others, the vehicle 102 includes the vehicle computing system 104 configured to receive the image data from the at least one camera (e.g., see cameras 118a to 118b). The vehicle computing system 104 can also be configured to determine, such as via the RSSS client 106, a risk score of the driver based on the received image data. The vehicle computing system 104 can also be configured to determine, such as via the RSSS client 106, a risk score of the driver for the time period of the request based on the received image data. The risk score can also be determined based on an AI technique. The AI technique can include an ANN, a decision tree, or another type of AI tool, or any combination thereof. The received biometric image data or a derivative thereof can be input for the AI technique in general or specifically for one or more of the aforesaid AI tools. For example, the received biometric data or a derivative thereof can be input for an ANN. The vehicle computing system 104 can also be configured to transmit the risk score of the driver to the customer so that the customer can decide whether to book the vehicle for a ride. The transmission of the risk score can be to a mobile device of the customer (e.g., see mobile devices 140 to 142 and mobile device 302).

In such embodiments and others, the vehicle 102 includes at least one sensor (e.g., see sensors 114a to 114b) configured to sense at least one non-visual biometric feature of the driver. The sensing of the at least one non-visual biometric feature of the driver can occur during the time period in which the images of the driver are recorded. The at least one sensor can also be configured to send non-visual biometric data derived from the at least one sensed non-visual biometric feature of the driver. The sensing of the at least one non-visual biometric feature of the driver can occur in response to a request for an evaluation of the driver by a customer determining whether to book the vehicle 102 for a ride. And, the sensing of the at least non-visual biometric feature can occur during the time period in which request is made by the customer. In other words, the request can occur during the time period of the sensing of the at least one non-visual biometric feature of the driver. And, the customer can make the request from a mobile device (e.g., see mobile devices 140 to 142 and mobile device 302).

In such embodiments and others, the vehicle computing system 104 can also be configured to receive the non-visual biometric data from the at least one sensor (e.g., see sensors 114a to 114b). The vehicle computing system 104 can also be configured to determine, such as via the RSSS client 106, a risk score of the driver based on the received non-visual biometric data. The vehicle computing system 104 can also be configured to determine, such as via the RSSS client 106, a risk score of the driver for the time period of the request based on the received non-visual biometric data. The risk score can also be determined based on an AI technique. The AI technique can include an ANN, a decision tree, or another type of AI tool, or any combination thereof. The received non-visual biometric data or a derivative thereof can be input for the AI technique in general or specifically for one or more of the aforesaid AI tools. For example, the received non-visual biometric data or a derivative thereof can be input for an ANN. In other words, the risk score can be determined based on the image data, the non-visual biometric data, or the ANN or another type of AI technique, or any combination thereof. In such examples, the received non-visual biometric data or a derivative thereof and/or the received image data or a derivative thereof can be input for the ANN or another type of AI technique. Also, in such examples, the vehicle computing system 104 can also be configured to transmit the risk score of the driver to the customer so that the customer can decide whether to book the vehicle for a ride and the transmission of the risk score can be to a mobile device of the customer (e.g., see mobile devices 140 to 142 and mobile device 302).

In such embodiments and others, the vehicle computing system 104 can be configured to receive, such as via the RSSS client 106, the biometric image data and/or the non-visual biometric data and determine, such as via the RSSS client 106, a risk score of the driver based on the received biometric data and an AI technique. The AI technique can include an ANN, a decision tree, or another type of AI tool, or any combination thereof. The received biometric data or a derivative thereof can be input for the AI technique in general or specifically for one or more of the aforesaid AI tools. The vehicle computing system 104 can also be configured to determine, such as via the RSSS client 106, whether to notify a potential customer for the vehicle 102 of the risk score based on the risk score exceeding a risk threshold. This can occur prior to the transmission of the risk score of the driver to the customer.

In such embodiments and others, the at least one sensor (e.g., see sensors 114a to 114b) can include a breathalyzer configured to sense blood alcohol content of the driver during the time period, and the at least one sensor can be configured to send data derived from the sensed blood alcohol content as at least part of the non-visual biometric data. In such embodiments and others, the at least one sensor (e.g., see sensors 114a to 114b) can include a thermometer configured to sense a body temperature of the driver during the time period, and the at least one sensor can be configured to send data derived from the sensed body temperature as at least part of the non-visual biometric data. In such embodiments and others, the at least one sensor (e.g., see sensors 114a to 114b) can include a microphone configured to transform sound from speech of the driver during the time period into an audio signal, and the at least one sensor can be configured to send data derived from the audio signal as at least part of the non-visual biometric data.

In some embodiments, the received image data sent from the at least one camera (e.g., see cameras 118a to 118b) can include information on a posture of the driver. And, in such embodiments and others, the received image data sent from the at least one camera can include information on facial characteristics of the driver.

In some embodiments, the vehicle computing system 104 of the vehicle 102 is configured to train the AI technique using supervised learning. The input for the supervised learning of the AI technique can include image data of images of sample drivers and risk scores determined by the customer for the images of the sample drivers. This way the AI technique (such as an ANN or a decision tree) can be customized and trained for the customer specifically. Also, the input for the supervised learning of the AI technique can include image data of images of sample drivers and risk scores determined by customers of the ridesharing service for the images of the sample drivers. This way the AI technique can be enhanced and trained for the customers of the service in general. The input for the supervised learning of the ANN can also include non-visual biometric information of the sample drivers and risk scores determined by the customer (or customers of the service in general) for the non-visual biometric information of the sample drivers.

In some embodiments, the vehicle computing system 104 of the vehicle 102 is configured to determine, such as via the RSSS client 106, biographical information of the driver of the vehicle based on at least the received biometric data and/or a database of drivers of the ridesharing service (such as a database which is connected to or a part of the RSSS server(s) 150). The database can store biographical information on registered drivers that are registered for the ridesharing service. And, the stored biographical information can include biometric characteristics of the registered drivers as well as at least one of criminal histories of the registered drivers, driving behavior histories of the registered drivers, or service or traffic violation histories of the registered drivers, or any combination thereof. In such embodiments and others, the vehicle computing system 104 of the vehicle 102 can be configured to determine the risk score of the driver based on the received biometric data, the AI technique, and the determined biographical information of the driver. The input for the AI technique can include the biometric data or a derivative thereof and/or the determined biographical information or a derivative thereof.

In some embodiments, the received biometric data received from the camera(s) and/or the sensor(s) (e.g., see cameras 118a to 118b and sensors 114a to 114b) can include information on a gait of the driver approaching the vehicle 102 before driving the vehicle, information of a posture of the driver while approaching the vehicle or while in the vehicle, or information on facial characteristics of the driver, or any combination thereof. The received biometric data can also include information on blood alcohol content of the driver, a body temperature of the driver, or speech of the driver, or any combination thereof.

The mobile devices described herein (e.g., see mobile devices 140 to 142 and mobile device 302) can include a user interface (e.g., see other components 316 of the mobile device 302 shown in FIG. 4), configured to output, such as via the RSSS client 106, the risk score. The risk score can be outputted by a UI of a mobile device to notify a customer when the vehicle computing system 104 of the vehicle 102 determines the risk score exceeds a risk threshold. The user interface of a mobile device can be configured to provide, such as via the RSSS client 106, a graphical user interface (GUI), a tactile user interface, or an auditory user interface, or any combination thereof. Also, embodiments described herein can include one or more user interfaces of any type, including tactile UI (touch), visual UI (sight), auditory UI (sound), olfactory UI (smell), equilibria UI (balance), and gustatory UI (taste).

Not depicted in FIG. 2, but depicted in FIG. 1, the vehicle 102 can include a camera that faces inwards into the cabin of the vehicle in one or more directions to have a field of view that covers at least a semicircle in a horizontal plane relative to the vehicle (e.g., see camera 16 and cameras 118a to 118b). And, the camera(s) can include the at least one camera configured to record the at least one image of the driver and to generate and send biometric data derived from the at least one image of the driver. In some embodiments, the camera(s) can have a field of view that covers at least a full circle in the horizontal plane to record at least one image of the driver in the vehicle 102 from any direction in the horizontal plane.

In some embodiments, the vehicle computing system 104 (such as via the RSSS client 106) can be configured to receive and process data (e.g., such as data including instructional data for the vehicle and its systems and/or data related to biometric information of the driver and/or biographical information of the driver stored in a database of the RSSS). For example, the data can be received, by the vehicle computing system 104 (such as via the RSSS client 106), from camera(s), sensors(s) and/or the RSSS server(s) 150 via a part of the network(s) 122, and then the received data can be processed for inclusion in other processing steps described herein. The received data can include information derived from at least linked risk score data, image data, sensed non-visual biometric data, temporal data, position data, or other contextual data sent from the vehicle 102 or other vehicles (e.g., see vehicles 130 to 132) regarding the driver. In some embodiments, the derivation of the received data and/or the later processing of the received data can be according to an AI technique, and the AI technique can be trained by a computing system of the RSSS, the vehicle 102, or a mobile device of the driver or customer (e.g., see mobile devices 140 to 142). In such embodiments and others, the mobile devices of the customers can include a user interface (such as a graphical user interface) configured to provide at least part of the received and processed data to the customers (e.g., see other components 316 of mobile device 302 depicted in FIG. 4, which can include a GUI).

The vehicle 102 includes vehicle electronics, including at least electronics for the controllable parts of the body, the controllable parts of the powertrain, and the controllable parts of the power steering. The vehicle 102 includes the controllable parts of the body and such parts and subsystems being connected to the body control module 108. The body includes at least a frame to support the powertrain. A chassis of the vehicle can be attached to the frame of the vehicle. The body can also include an interior for at least one driver or passenger. The interior can include seats. The controllable parts of the body can also include one or more power doors and/or one or more power windows. The body can also include any other known parts of a vehicle body. And, the controllable parts of the body can also include a convertible top, sunroof, power seats, and/or any other type of controllable part of a body of a vehicle. The body control module 108 can control the controllable parts of the body. Also, the vehicle 102 also includes the controllable parts of the powertrain. The controllable parts of the powertrain and its parts and subsystems are connected to the powertrain control module 110. The controllable parts of the powertrain can include at least an engine, transmission, drive shafts, suspension and steering systems, and powertrain electrical systems. The powertrain can also include any other known parts of a vehicle powertrain and the controllable parts of the powertrain can include any other known controllable parts of a powertrain. Also, power steering parts that are controllable can be controlled via the power steering control unit 112.

The plurality of sensors (e.g., see sensors 114a to 114b) and/or the plurality of cameras (e.g., see cameras 118a to 118b) of the vehicle 102 can include any type of sensor or camera respectively configured to sense and/or record one or more features or characteristics of a driver within the cabin of the vehicle 102 (e.g., see cabin 12) or of the surroundings of the vehicle 102, such as when the driver is approaching the vehicle in the vehicle's surroundings. A sensor or a camera of the vehicle 102 can also be configured to output the generated data corresponding to the one or more features or characteristics of the driver. Any one of the plurality of sensors or cameras can also be configured to send, such as via the CAN bus 120, the generated data corresponding to the one or more features or characteristics of the driver to the vehicle computing system 104 or other electronic circuitry of the vehicle 102. The sending of the data to other electronic circuitry of the vehicle 102 can be useful when a driver is drunk, tired, sick, or inhibited from driving well in another way. For example, the data or a derivative thereof can be sent to the body control module 108 to lock or position the driver seat to hint to the driver that he or she should not be driving, the powertrain control module 110 to prevent the engine from being turned on, and/or the power steering control unit 112 to lock the wheels in a direction moving towards a parked position of the vehicle, in response to a driver that is drunk, tired, sick, or inhibited from driving well in another way.

A set of mechanical components for controlling the driving of the vehicle 102 can include: (1) a brake mechanism on wheels of the vehicle (for stopping the spinning of the wheels), (2) a throttle mechanism on an engine or motor of the vehicle (for regulation of how much gas goes into the engine, or how much electrical current goes into the motor), which determines how fast a driving shaft can spin and thus how fast the vehicle can run, and (3) a steering mechanism for the direction of front wheels of the vehicle (for example, so the vehicle goes in the direction of where the wheels are pointing to). These mechanisms can control the braking (or deacceleration), acceleration (or throttling), and steering of the vehicle 102. The driver can indirectly control these mechanisms by UI elements (e.g., see other components 216 of vehicle 202 shown in FIG. 3) that can be operated upon by the user, which are typically the brake pedal, the acceleration pedal, and the steering wheel. The pedals and the steering wheel are not necessarily mechanically connected to the driving mechanisms for braking, acceleration and steering. Such parts can have or be proximate to sensors that measure how much the driver has pressed on the pedals and/or turned the steering wheel. The sensed control input is transmitted to the control units over wires (and thus can be drive-by-wire). Such control units can include body control module 108 or 220, powertrain control module 110 or 222, power steering control unit 112 or 224, battery management system 226, etc. Such output can also be sensed and/or recorded by the sensors and cameras described herein as well (e.g., see sensors 114a to 114b or 217a to 217b and cameras 118a to 118b or 219a to 219b). And, the output of the sensors and cameras can be further processed, such as by the RSSS client 106, and then reported to the server(s) 150 of the RSSS for cumulative data processing of contextual data related to the driver of the vehicle.

In a vehicle, such as vehicle 102 or 202, a driver can control the vehicle via physical control elements (e.g., steering wheel, brake pedal, gas pedal, paddle gear shifter, etc.) that interface drive components via mechanical linkages and some electromechanical linkages. However, more and more vehicles currently have the control elements interface the mechanical powertrain elements (e.g., brake system, steering mechanisms, drive train, etc.) via electronic control elements or modules (e.g., electronic control units or ECUs). The electronic control elements or modules can be a part of drive-by-wire technology. Drive-by-wire technology can include electrical or electromechanical systems for performing vehicle functions traditionally achieved by mechanical linkages. The technology can replace the traditional mechanical control systems with electronic control systems using electromechanical actuators and human-machine interfaces such as pedal and steering feel emulators. Components such as the steering column, intermediate shafts, pumps, hoses, belts, coolers and vacuum servos and master cylinders can be eliminated from the vehicle. There are varying degrees and types of drive-by-wire technology. Vehicles, such as vehicles 102 and 202, having drive-by-wire technology can include a modulator (such as a modulator including or being a part of an ECU and/or an advance driver assistance system or ADAS) that receives input from a user or driver (such as via more conventional controls or via drive-by-wire controls or some combination thereof). The modulator can then use the input of the driver to modulate the input or transform it to match input of a "safe driver".

In some embodiments, the electronic circuitry of a vehicle (e.g., see vehicles 102 and 202), which can include or be a part of the computing system of the vehicle, can include at least one of engine electronics, transmission electronics, chassis electronics, driver or passenger environment and comfort electronics, in-vehicle entertainment electronics, in-vehicle safety electronics, or navigation system electronics, or any combination thereof (e.g., see body control modules 108 and 220, powertrain control modules 110 and 222, power steering control units 112 and 224, battery management system 226, and infotainment electronics 228 shown in FIGS. 2 and 3 respectively). In some embodiments, the electronic circuitry of the vehicle can include electronics for an automated driving system.

As shown in FIG. 3, the networked system 100 can include at least vehicles 130 to 132 and vehicle 202 which includes at least a vehicle computing system 204, a body (not depicted) having an interior (not depicted), a powertrain (not depicted), a climate control system (not depicted), and an infotainment system (not depicted). The vehicle 202 can include other vehicle parts as well.

The vehicle computing system 204, which can have similar structure and/or functionality as the vehicle computing system 104, can be connected to communications network(s) 122 that can include at least a local to device network such as Bluetooth or the like, a wide area network (WAN), a local area network (LAN), an intranet, a mobile wireless network such as 4G or 5G, an extranet, the Internet, and/or any combination thereof. The vehicle computing system 204 can be a machine capable of executing a set of instructions (sequential or otherwise) that specify actions to be taken by that machine. Also, while a single machine is illustrated for the vehicle computing system 204, the term "machine" shall also be taken to include any collection of machines that individually or jointly execute a set (or multiple sets) of instructions to perform a methodology or operation. And, it can include at least a bus (e.g., see bus 206) and/or motherboard, one or more controllers (such as one or more CPUs, e.g., see controller 208), a main memory (e.g., see memory 210) that can include temporary data storage, at least one type of network interface (e.g., see network interface 212), a storage system (e.g., see data storage system 214) that can include permanent data storage, and/or any combination thereof. In some multi-device embodiments, one device can complete some parts of the methods described herein, then send the result of completion over a network to another device such that another device can continue with other steps of the methods described herein.

FIG. 3 also illustrates example parts of the vehicle computing system 204 that can include and implement the RSSS client 106. The vehicle computing system 204 can be communicatively coupled to the network(s) 122 as shown. The vehicle computing system 204 includes at least a bus 206, a controller 208 (such as a CPU) that can execute instructions of the RSSS client 106, memory 210 that can hold the instructions of the RSSS client 106 for execution, a network interface 212, a data storage system 214 that can store instructions for the RSSS client 106, and other components 216—which can be any type of components found in mobile or computing devices such as GPS components, I/O components such as a camera and various types of user interface components (which can include one or more of the plurality of UI elements described herein) and sensors (which can include one or more of the plurality of sensors described herein). The other components 216 can include one or more user interfaces (e.g., GUIs, auditory user interfaces, tactile user interfaces, car controls, etc.), displays, different types of sensors, tactile, audio and/or visual input/output devices, additional application-specific memory, one or more additional controllers (e.g., GPU), or any combination thereof. The vehicle computing system 204 can also include sensor and camera interfaces that are configured to interface sensors and cameras of the vehicle 202 which can be one or more of any of the sensors or cameras described herein (e.g., see sensors 217a to 217b and cameras 219a to 219b). The bus 206 communicatively couples the controller 208, the memory 210, the network interface 212, the data storage system 214, the other components 216, and the sensors and cameras as well as sensor and camera interfaces in some embodiments. The vehicle computing system 204 includes a computer system that includes at least controller 208, memory 210 (e.g., read-only memory (ROM), flash memory, dynamic random-access memory (DRAM) such as synchronous DRAM (SDRAM) or Rambus DRAM (RDRAM), static random-access memory (SRAM), cross-point memory, crossbar memory, etc.), and data storage system 214, which communicate with each other via bus 206 (which can include multiple buses).

In some embodiments, the vehicle computing system 204 can include a set of instructions, for causing a machine to perform any one or more of the methodologies discussed herein, when executed. In such embodiments, the machine can be connected (e.g., networked via network interface 212) to other machines in a LAN, an intranet, an extranet, and/or the Internet (e.g., network(s) 122). The machine can operate in the capacity of a server or a client machine in client-server network environment, as a peer machine in a peer-to-peer (or distributed) network environment, or as a server or a client machine in a cloud computing infrastructure or environment.

Controller 208 represents one or more general-purpose processing devices such as a microprocessor, a central processing unit, or the like. More particularly, the processing device can be a complex instruction set computing (CISC) microprocessor, reduced instruction set computing (RISC) microprocessor, very long instruction word (VLIW) microprocessor, single instruction multiple data (SIMD), multiple instructions multiple data (MIMD), or a processor implementing other instruction sets, or processors implementing a combination of instruction sets. Controller 208 can also be one or more special-purpose processing devices such as an ASIC, a programmable logic such as an FPGA, a digital signal processor (DSP), network processor, or the like. Controller 208 is configured to execute instructions for performing the operations and steps discussed herein. Controller 208 can further include a network interface device such as network interface 212 to communicate over one or more communications network (such as network(s) 122).

The data storage system 214 can include a machine-readable storage medium (also known as a computer-readable medium) on which is stored one or more sets of instructions or software embodying any one or more of the methodologies or functions described herein. The data storage system 214 can have execution capabilities such as it can at least partly execute instructions residing in the data storage system. The instructions can also reside, completely or at least partially, within the memory 210 and/or within the controller 208 during execution thereof by the computer system, the memory 210 and the controller 208 also constituting machine-readable storage media. The memory 210 can be or include main memory of the system 204. The memory 210 can have execution capabilities such as it can at least partly execute instructions residing in the memory.

The vehicle 202 can also have vehicle body control module 220 of the body, powertrain control module 222 of the powertrain, a power steering control unit 224, a battery management system 226, infotainment electronics 228 of the infotainment system, and a CAN bus 218 that connects at least the vehicle computing system 204, the vehicle body control module, the powertrain control module, the power steering control unit, the battery management system, and the infotainment electronics. Also, as shown, the vehicle 202 is connected to the network(s) 122 via the vehicle computing system 204. Also, shown, vehicles 130 to 132 and mobile devices 140 to 142 are connected to the network(s) 122. And, thus, are communicatively coupled to the vehicle 202.

The vehicle 202 is also shown having the plurality of sensors (e.g., see sensors 217a to 217b) and the plurality of cameras (e.g., see cameras 219a to 219b), which can be part of the vehicle computing system 204. In some embodiments, the CAN bus 218 can connect the plurality of sensors and the plurality of cameras, the vehicle computing system 204, the vehicle body control module, the powertrain control module, the power steering control unit, the battery management system, and the infotainment electronics to at least the vehicle computing system 204. The plurality of sensors and the plurality of cameras can be connected to the vehicle computing system 204 via sensor and camera interfaces of the computing system.

As shown in FIG. 4, the networked system 100 can include at least a mobile device 302 as well as mobile devices 140 to 142. The mobile device 302, which can have somewhat similar structure and/or functionality as the vehicle computing system 104 or 204, can be connected to communications network(s) 122. And, thus, be connected to vehicles 102, 202, and 130 to 132 as well as mobile devices 140 to 142. The mobile device 302 (or mobile device 140 or 142) can include one or more of the plurality of sensors mentioned herein, one or more of the plurality of UI elements mentioned herein, a GPS device, and/or one or more of the plurality of cameras mentioned herein. Thus, the mobile device 302 (or mobile device 140 or 142) can act similarly to vehicle computing system 104 or 204 and can host and run the RSSS client 106.

The mobile device 302, depending on the embodiment, can be or include a mobile device or the like, e.g., a smartphone, tablet computer, IoT device, smart television, smart watch, glasses or other smart household appliance, in-vehicle information system, wearable smart device, game console, PC, digital camera, or any combination thereof. As shown, the mobile device 302 can be connected to communications network(s) 122 that includes at least a local to device network such as Bluetooth or the like, a wide area network (WAN), a local area network (LAN), an intranet, a mobile wireless network such as 4G or 5G, an extranet, the Internet, and/or any combination thereof.

Each of the mobile devices described herein can be or be replaced by a personal computer (PC), a tablet PC, a set-top box (STB), a Personal Digital Assistant (PDA), a cellular telephone, a web appliance, a server, a network router, a switch or bridge, or any machine capable of executing a set of instructions (sequential or otherwise) that specify actions to be taken by that machine. The computing systems of the vehicles described herein can be a machine capable of executing a set of instructions (sequential or otherwise) that specify actions to be taken by that machine.

Also, while a single machine is illustrated for the computing systems and mobile devices described herein, the term "machine" shall also be taken to include any collection of machines that individually or jointly execute a set (or multiple sets) of instructions to perform any one or more of the methodologies or operations discussed herein. And, each of the illustrated mobile devices can each include at least a bus and/or motherboard, one or more controllers (such as one or more CPUs), a main memory that can include temporary data storage, at least one type of network interface, a storage system that can include permanent data storage, and/or any combination thereof. In some multi-device embodiments, one device can complete some parts of the methods described herein, then send the result of completion over a network to another device such that another device can continue with other steps of the methods described herein.

FIG. 4 also illustrates example parts of the mobile device 302, in accordance with some embodiments of the present disclosure. The mobile device 302 can be communicatively coupled to the network(s) 122 as shown. The mobile device 302 includes at least a bus 306, a controller 308 (such as a CPU), memory 310, a network interface 312, a data storage system 314, and other components 316 (which can be any type of components found in mobile or computing devices such as GPS components, I/O components such various types of user interface components, and sensors (such as biometric sensors) as well as one or more cameras). The other components 316 can include one or more user interfaces (e.g., GUIs, auditory user interfaces, tactile user interfaces, etc.), displays, different types of sensors, tactile (such as biometric sensors), audio and/or visual input/output devices, additional application-specific memory, one or more additional controllers (e.g., GPU), or any combination thereof. The bus 306 communicatively couples the controller 308, the memory 310, the network interface 312, the data storage system 314 and the other components 316. The mobile device 302 includes a computer system that includes at least controller 308, memory 310 (e.g., read-only memory (ROM), flash memory, dynamic random-access memory (DRAM) such as synchronous DRAM (SDRAM) or Rambus DRAM (RDRAM), static random-access memory (SRAM), cross-point memory, crossbar memory, etc.), and data storage system 314, which communicate with each other via bus 306 (which can include multiple buses).

To put it another way, FIG. 4 is a block diagram of mobile device 302 that has a computer system in which embodiments of the present disclosure can operate. In some embodiments, the computer system can include a set of instructions, for causing a machine to perform some of the methodologies discussed herein, when executed. In such embodiments, the machine can be connected (e.g., networked via network interface 312) to other machines in a LAN, an intranet, an extranet, and/or the Internet (e.g., network(s) 122). The machine can operate in the capacity of a server or a client machine in client-server network environment, as a peer machine in a peer-to-peer (or distributed) network environment, or as a server or a client machine in a cloud computing infrastructure or environment.

Controller 308 represents one or more general-purpose processing devices such as a microprocessor, a central processing unit, or the like. More particularly, the processing device can be a complex instruction set computing (CISC) microprocessor, reduced instruction set computing (RISC) microprocessor, very long instruction word (VLIW) microprocessor, single instruction multiple data (SIMD), multiple instructions multiple data (MIMD), or a processor implementing other instruction sets, or processors implementing a combination of instruction sets. Controller 308 can also be one or more special-purpose processing devices such as an ASIC, a programmable logic such as an FPGA, a digital signal processor (DSP), network processor, or the like. Controller 308 is configured to execute instructions for performing the operations and steps discussed herein. Controller 308 can further include a network interface device such as network interface 312 to communicate over one or more communications network (such as network(s) 122).

The data storage system 314 can include a machine-readable storage medium (also known as a computer-readable medium) on which is stored one or more sets of instructions or software embodying any one or more of the methodologies or functions described herein. The data storage system 314 can have execution capabilities such as it can at least partly execute instructions residing in the data storage system. The instructions can also reside, completely or at least partially, within the memory 310 and/or within the controller 308 during execution thereof by the computer system, the memory 310 and the controller 308 also constituting machine-readable storage media. The memory 310 can be or include main memory of the device 302. The memory 310 can have execution capabilities such as it can at least partly execute instructions residing in the memory.

While the memory, controller, and data storage parts are shown in example embodiments to each be a single part, each part should be taken to include a single part or multiple parts that can store the instructions and perform their respective operations. The term "machine-readable storage medium" shall also be taken to include any medium that is capable of storing or encoding a set of instructions for execution by the machine and that cause the machine to perform any one or more of the methodologies of the present disclosure. The term "machine-readable storage medium" shall accordingly be taken to include, but not be limited to, solid-state memories, optical media, and magnetic media.

As shown in FIG. 4, the mobile device 302 can include a user interface (e.g., see other components 316). The user interface can be configured to provide a graphical user interface (GUI), a tactile user interface, or an auditory user interface, or any combination thereof. For example, the user interface can be or include a display connected to at least one of a wearable structure, a computing device, or a camera or any combination thereof that can also be a part of the mobile device 302, and the display can be configured to provide a GUI. Also, embodiments described herein can include one or more user interfaces of any type, including tactile UI (touch), visual UI (sight), auditory UI (sound), olfactory UI (smell), equilibria UI (balance), and gustatory UI (taste).

Figure 5:
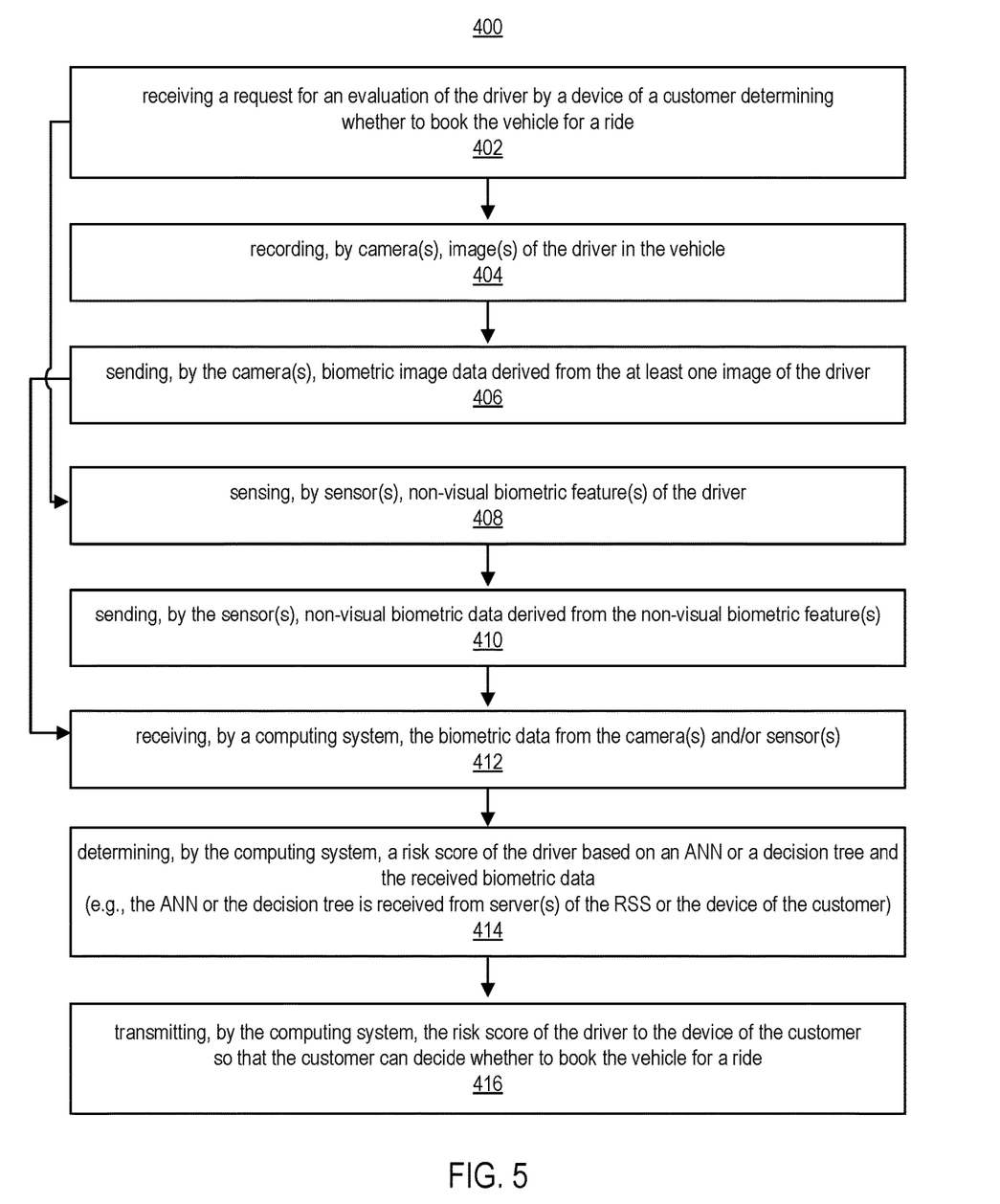
FIGS. 5 to 6 illustrate flow diagrams of example operations that can be performed by aspects of the vehicle shown in FIG. 1 or the networked system depicted in FIGS. 2 to 4, in accordance with some embodiments of the present disclosure.

FIG. 5 illustrates a flow diagram of example operations of method 400 that can be performed by aspects of the vehicle 10 depicted in FIG. 1 as well as the networked system 100 depicted in FIGS. 2 to 4, in accordance with some embodiments of the present disclosure. For example, the method 400 can be performed by a computing system and/or other parts of any vehicle and/or mobile device depicted in FIGS. 1 to 4.

In FIG. 5, the method 400 begins at step 402 with receiving during a time period, by a vehicle or a mobile device of a driver of the vehicle, a request for an evaluation of the driver by a mobile device of a customer determining whether to book the vehicle for a ride. At step 404, the method 400 continues with recording, by one or more cameras of the vehicle (or one or more cameras of a mobile device of the driver in the vehicle), one or more images of the driver in the vehicle during the time period. At step 406, the method 400 continues with sending, by the camera(s), biometric image data derived from the at least one image of the driver. At step 408, the method 400 continues with sensing, by one or more sensors of the vehicle (or one or more sensors of a mobile device of the driver in the vehicle), one or more non-visual biometric features of the driver during the time period. At step 410, the method 400 continues with sending, by the sensor(s), non-visual biometric data derived from the non-visual biometric feature(s). At step 412, the method 400 continues with receiving, by a computing system of the vehicle (or of a mobile device in the vehicle), the biometric data from the camera(s) and/or sensor(s). At step 414, the method 400 continues with determining, by the computing system, a risk score of the driver for the time period based on an ANN or a decision tree and the received biometric data (e.g., the ANN or the decision tree is received from server(s) of the RSS or the mobile device of the customer). At step 416, the method 400 continues with transmitting, by the computing system, the risk score of the driver to the mobile device of the customer so that the customer can decide whether to book the vehicle for a ride.

Figure 6:
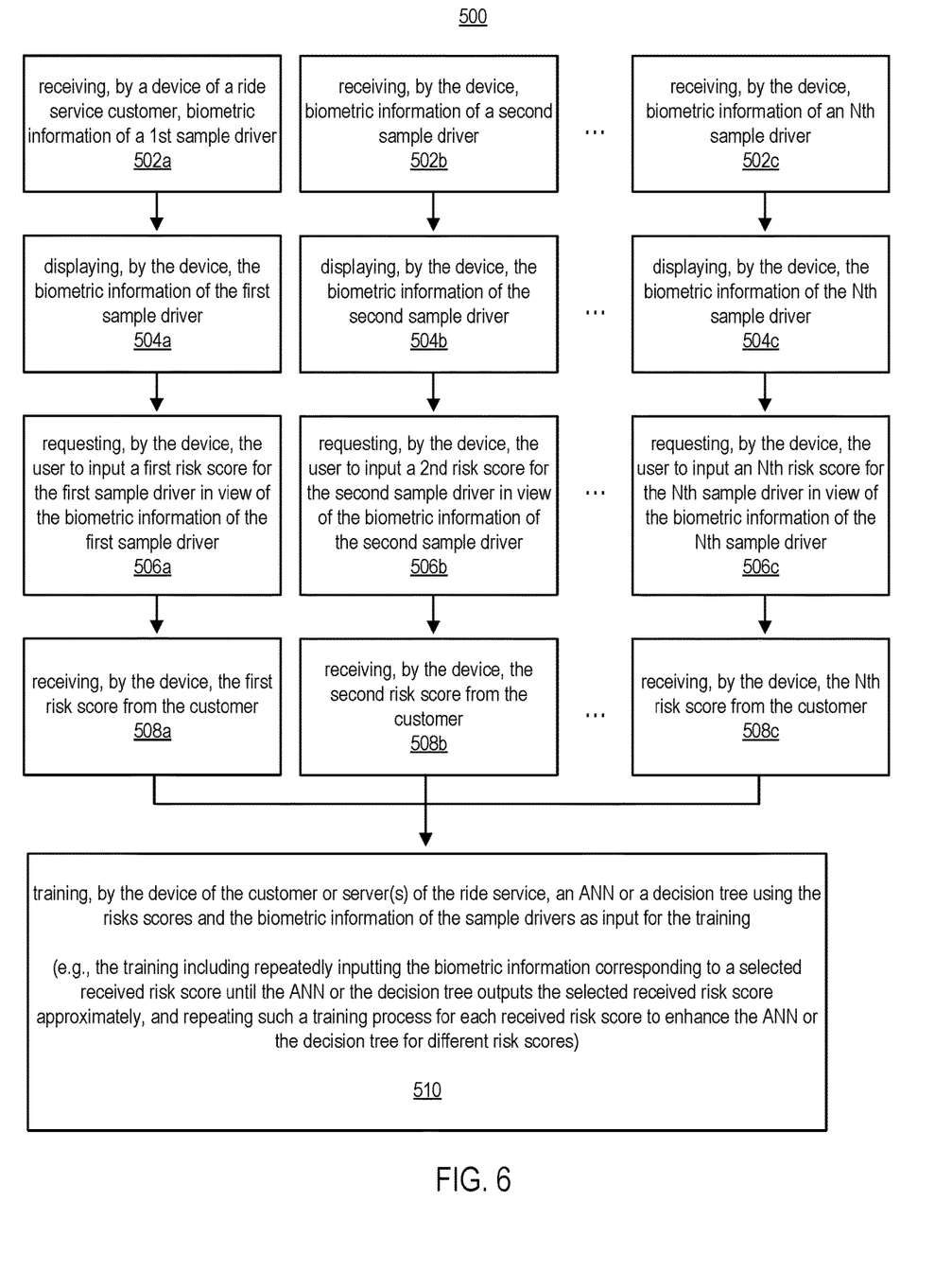

FIG. 6 illustrates a flow diagram of example operations of method 500 that can be performed by aspects of the vehicle 10 depicted in FIG. 1 as well as the networked system 100 depicted in FIGS. 2 to 4, in accordance with some embodiments of the present disclosure. For example, the method 500 can be performed by a computing system and/or other parts of any vehicle and/or mobile device depicted in FIGS. 1 to 4.

In FIG. 6, the method 500 can begin at step 502a with receiving, by a mobile device of a ride service customer, biometric information of a first sample driver. The method 500 can also begin at step 502b with receiving, by the mobile device, biometric information of a second sample driver. The method 500 can also begin at step 502c with receiving, by the mobile device, biometric information of another sample driver. As shown, the method 500 can begin with receiving at least three different instances of biometric information of at least three respective sample drivers. The receiving of the biometric information can occur simultaneously or in a sequence.

At step 504a, the method 500 continues with displaying, by the mobile device, the biometric information of the first sample driver. At step 504b, the method 500 continues with displaying, by the mobile device, the biometric information of the second sample driver. At step 504c, the method 500 continues with displaying, by the mobile device, the biometric information of the other sample driver. As shown, the method 500 continues with displaying at least three different instances of biometric information of at least three respective sample drivers. The displaying of the biometric information can occur simultaneously or in a sequence.

At step 506a, the method 500 continues with requesting, by the mobile device, the user to input a first risk score for the first sample driver in view of the biometric information of the first sample driver. At step 506b, the method 500 continues with requesting, by the mobile device, the user to input a second risk score for the second sample driver in view of the biometric information of the second sample driver. At step 506c, the method 500 continues with requesting, by the mobile device, the user to input another risk score for the other sample driver in view of the biometric information of the other sample driver. As shown, the method 500 continues with requesting the user to input risk scores for at least three different respective sample drivers. The requesting for the user to input risk scores for at least three different respective sample drivers can occur simultaneously or in a sequence.

At step 508a, the method 500 continues with receiving, by the mobile device, the first risk score from the customer. At step 508b, the method 500 continues with receiving, by the mobile device, the second risk score from the customer. At step 508c, the method 500 continues with receiving, by the mobile device, the other risk score from the customer. As shown, the method 500 continues with receiving the risk scores from the customer for at least three different respective sample drivers. The receiving the risk scores from the customer can occur simultaneously or in a sequence.

At step 510, the method 500 continues with training, by the mobile device of the customer or one or more servers of the ride service, an ANN or a decision tree using the risks scores and the biometric information of the sample drivers as input for the training. For example, the training at step 510 can include repeatedly inputting the biometric information corresponding to a selected received risk score until the ANN or the decision tree outputs the selected received risk score approximately, and repeating such a training process for each received risk score to enhance the ANN or the decision tree for different risk scores.

In some embodiments, it is to be understood that the steps of methods 400 and 500 can be implemented as a continuous process such as each step can run independently by monitoring input data, performing operations and outputting data to the subsequent step. Also, such steps for each method can be implemented as discrete-event processes such as each step can be triggered on the events it is supposed to trigger and produce a certain output. It is to be also understood that each figure of FIGS. 5 to 6 represents a minimal method within a possibly larger method of a computer system more complex than the ones presented partly in FIGS. 2 to 4. Thus, the steps depicted in each figure of FIGS. 5 to 6 can be combined with other steps feeding in from and out to other steps associated with a larger method of a more complex system.

It is to be understood that a vehicle described herein can be any type of vehicle unless the vehicle is specified otherwise. Vehicles can include cars, trucks, boats, and airplanes, as well as vehicles or vehicular equipment for military, construction, farming, or recreational use. Electronics used by vehicles, vehicle parts, or drivers or passengers of a vehicle can be considered vehicle electronics. Vehicle electronics can include electronics for engine management, ignition, radio, carputers, telematics, in-car entertainment systems, and other parts of a vehicle. Vehicle electronics can be used with or by ignition and engine and transmission control, which can be found in vehicles with internal combustion powered machinery such as gas-powered cars, trucks, motorcycles, boats, planes, military vehicles, forklifts, tractors and excavators. Also, vehicle electronics can be used by or with related elements for control of electrical systems found in hybrid and electric vehicles such as hybrid or electric automobiles. For example, electric vehicles can use power electronics for the main propulsion motor control, as well as managing the battery system. And, autonomous vehicles almost entirely rely on vehicle electronics.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. The present disclosure can refer to the action and processes of a computer system, or similar electronic computing device, that manipulates and transforms data represented as physical (electronic) quantities within the computer system's registers and memories into other data similarly represented as physical quantities within the computer system memories or registers or other such information storage systems.

The present disclosure also relates to an apparatus for performing the operations herein. This apparatus can be specially constructed for the intended purposes, or it can include a general-purpose computer selectively activated or reconfigured by a computer program stored in the computer. Such a computer program can be stored in a computer readable storage medium, such as any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

The algorithms and displays presented herein are not inherently related to any particular computer or other apparatus. Various general-purpose systems can be used with programs in accordance with the teachings herein, or it can prove convenient to construct a more specialized apparatus to perform the method. The structure for a variety of these systems will appear as set forth in the description below. In addition, the present disclosure is not described with reference to any particular programming language. It will be appreciated that a variety of programming languages can be used to implement the teachings of the disclosure as described herein.

The present disclosure can be provided as a computer program product, or software, that can include a machine-readable medium having stored thereon instructions, which can be used to program a computer system (or other electronic devices) to perform a process according to the present disclosure. A machine-readable medium includes any mechanism for storing information in a form readable by a machine (e.g., a computer). In some embodiments, a machine-readable (e.g., computer-readable) medium includes a machine (e.g., a computer) readable storage medium such as a read only memory ("ROM"), random access memory ("RAM"), magnetic disk storage media, optical storage media, flash memory components, etc.

In the foregoing specification, embodiments of the disclosure have been described with reference to specific example embodiments thereof. It will be evident that various modifications can be made thereto without departing from the broader spirit and scope of embodiments of the disclosure as set forth in the following claims. The specification and drawings are, accordingly, to be regarded in an illustrative sense rather than a restrictive sense.

What is claimed is:

1. An apparatus comprising:
   at least one processing device; and
   memory containing instructions configured to instruct the at least one processing device to:
      receive image data provided by at least one camera of a vehicle, wherein the image data is derived from at least one image of a driver in the vehicle, and wherein the at least one camera is configured to record the at least one image in response to a request by a first user of a first mobile device external to the vehicle;
      determine, using an artificial neural network (ANN) having an input based on the received image data, a risk score of the driver, wherein the ANN has been trained using prior images of drivers and corresponding risk scores; and
      cause transmission to the first mobile device of a communication for providing, based on the determined risk score, a display on the first mobile device.

2. The apparatus of claim 1, further comprising at least one sensor, wherein the instructions are further configured to instruct the at least one processing device to:
   receive biometric data provided by the at least one sensor;
   wherein the input to the ANN is further based on the received biometric data.

3. The apparatus of claim 2, wherein the at least one sensor comprises a breathalyzer configured to sense a blood alcohol content of the driver.

4. The apparatus of claim 2, wherein the at least one sensor comprises a thermometer configured to sense a body temperature of the driver.

5. The apparatus of claim 2, wherein the at least one sensor comprises a microphone.

6. The apparatus of claim 1, wherein the display on the first mobile device includes biometric data regarding the driver.

7. The apparatus of claim 1, wherein the received image data comprises data regarding at least one of a posture or facial characteristic of the driver.

8. The apparatus of claim 1, wherein the instructions are further configured to instruct the at least one processing device to train, based on data from the at least one camera, the ANN.

9. The apparatus of claim 8, wherein the input for the ANN is further based on data regarding images of first drivers for other vehicles, and corresponding risk scores determined by users for the first drivers.

10. The apparatus of claim 9, wherein the input for the ANN is further based on biometric data of the first drivers.

11. A system comprising:
    at least one camera configured to record at least one image of a driver in a vehicle, wherein the at least one image is recorded in response to a request by a user of a mobile device external to the vehicle; and
    a computing system configured to:
      receive image data derived from the at least one image;
      determine, using an artificial neural network (ANN) or decision tree having an input based on the received image data, a risk score of the driver, wherein the ANN or decision tree has been trained using prior images of the driver and corresponding risk scores; and
      transmit, to the mobile device, a communication for providing, based on the determined risk score, a display on the mobile device.

12. The system of claim 11, further comprising at least one sensor, wherein the instructions are further configured to instruct the at least one processing device to:
    receive biometric data from the at least one sensor;
    wherein the input to the ANN or decision tree is further based on the received biometric data.

13. The system of claim 12, where the at least one sensor comprises a breathalyzer configured to sense a blood alcohol content of the driver, and provide data derived from the sensed blood alcohol content as part of the biometric data.

14. The system of claim 12, wherein the at least one sensor comprises a thermometer configured to sense a body temperature of the driver, and provide data derived from the sensed body temperature as part of the biometric data.

15. The system of claim 12, wherein the at least one sensor comprises a microphone configured to transform sound from speech of the driver into an audio signal, and provide data derived from the audio signal as part of the biometric data.

16. The system of claim 11, wherein the received image data comprises data regarding a posture of the driver.

17. The system of claim 11, wherein the received image data comprises facial characteristics of the driver.

18. The system of claim 11, wherein the computing system is further configured to train the ANN or decision tree using supervised learning.

19. The system of claim 11, wherein the input for the ANN or decision tree is further based on data regarding images of drivers for other vehicles.

20. A method comprising:
- receiving, by at least one memory device and over a bus from at least one camera, image data derived from at least one image of a driver in a vehicle, wherein the at least one camera records the at least one image in response to a request by a user of a mobile device external to the vehicle;
- determining, by at least one processing device and using an artificial neural network (ANN) having an input based on the image data, a risk score of the driver, wherein the ANN has been trained using prior images of drivers, including the driver, and corresponding risk scores; and
- causing, based on the determined risk score, transmission of a communication to the mobile device regarding the driver.

* * * * *